United States Patent
Goto et al.

(10) Patent No.: US 8,670,817 B2
(45) Date of Patent: *Mar. 11, 2014

(54) FLUOROSCOPIC IMAGING SYSTEM

(75) Inventors: Masashi Goto, Kanagawa (JP); Shigeru Nemoto, Tokyo (JP)

(73) Assignees: Resource One Inc, Kanagawa (JP); Nemoto Kyorindo Co., Ltd., Tokyo (JP)

( * ) Notice: Subject to any disclaimer, the term of this patent is extended or adjusted under 35 U.S.C. 154(b) by 1247 days.

This patent is subject to a terminal disclaimer.

(21) Appl. No.: 12/295,766

(22) PCT Filed: Apr. 2, 2007

(86) PCT No.: PCT/JP2007/000354
§ 371 (c)(1),
(2), (4) Date: Oct. 2, 2008

(87) PCT Pub. No.: WO2007/125638
PCT Pub. Date: Nov. 8, 2007

(65) Prior Publication Data
US 2009/0163802 A1    Jun. 25, 2009

(30) Foreign Application Priority Data
Apr. 5, 2006 (JP) ................................ 2006-104355

(51) Int. Cl.
*A61B 6/00* (2006.01)
(52) U.S. Cl.
USPC ........... 600/431; 600/420; 600/432; 382/294; 382/296
(58) Field of Classification Search
USPC ................... 600/420, 431, 432; 382/294, 296
See application file for complete search history.

(56) References Cited

U.S. PATENT DOCUMENTS

| | | | | |
|---|---|---|---|---|
| 7,379,655 | B1* | 5/2008 | Koyabu et al. | 386/296 |
| 7,430,341 | B2* | 9/2008 | Takeo | 382/294 |
| 2004/0064040 | A1* | 4/2004 | Masuda et al. | 600/431 |
| 2004/0162484 | A1* | 8/2004 | Nemoto | 600/420 |
| 2004/0199076 | A1* | 10/2004 | Nemoto | 600/432 |
| 2006/0002633 | A1* | 1/2006 | Takeo | 382/294 |
| 2006/0064321 | A1 | 3/2006 | Sasano et al. | |
| 2006/0074294 | A1* | 4/2006 | Williams et al. | 600/420 |

(Continued)

FOREIGN PATENT DOCUMENTS

| JP | 2001-101320 | 4/2001 |
|---|---|---|
| JP | 2004-298550 | 10/2004 |

(Continued)

OTHER PUBLICATIONS

International Search Report for PCT/JP2007/000354 dated Jul. 10, 2007.

*Primary Examiner* — Baisakhi Roy
(74) *Attorney, Agent, or Firm* — Rankin, Hill & Clark LLP

(57) ABSTRACT

A liquid injector (400) injects a medical liquid into a patient whose fluoroscopic image data is to be picked up, and generates injection history data corresponding to the injection. A control box (500) allocates identification data associated with the fluoroscopic image data to the injection history data, and PACS (300) stores the fluoroscopic image data and the injection history data allocated with the identification data. The injection history data is also stored in association with the fluoroscopic image data to be stored, and hence the injection history data can also be confirmed when viewing the fluoroscopic image data.

22 Claims, 9 Drawing Sheets

(56) References Cited

U.S. PATENT DOCUMENTS

2006/0184122 A1    8/2006  Nemoto
2007/0225601 A1*   9/2007  Uber et al. .................... 600/431
2008/0045930 A1*   2/2008  Makin et al. ................ 604/890.1
2010/0160776 A1*   6/2010  Goto et al. .................... 600/431
2010/0174181 A1*   7/2010  Nemoto ........................ 600/431

FOREIGN PATENT DOCUMENTS

| JP | 2005-198808 | 7/2005 |
| JP | 2006-061278 | 3/2006 |
| WO | 2005/007220 | 1/2005 |

* cited by examiner

FLUOROSCOPIC IMAGING SYSTEM

TECHNICAL FIELD

The present invention relates to a fluoroscopic imaging system that includes an imaging diagnostic apparatus, a liquid injector and an image viewer, employed for picking up fluoroscopic image data from a patient to whom a medical liquid is injected, and to display such image.

BACKGROUND ART

Fluoroscopic imaging equipments currently available for picking up a tomographic image, which is fluoroscopic image data of a patient, includes a Computed Tomography (CT) scanner, a Magnetic Resonance Imaging (MRI) equipment, a Positron Emission Tomography (PET) equipment, and an ultrasonic diagnostic equipment. Also, medical equipments that pick up a vascular image, which is another fluoroscopic image data of the patient, include a CT angiographic equipment, a Magnetic Resonance Angiographic (MRA) equipment, and so forth.

When one of such equipments is used, the patient often undergoes an injection of a medical liquid (or simply liquid as the case may be), also called a medical fluid, such as a contrast medium or physiological saline, and liquid injector that automatically execute the injection are currently in practical use. A popular liquid injector retains a liquid syringe loaded with the liquid, and a piston member is press-inserted into the cylinder member of the syringe to thereby inject the liquid into the patient's body.

Although the imaging diagnostic apparatus can work on a stand-alone basis, normally a fluoroscopic imaging system is constituted, including the imaging diagnostic apparatus as part thereof. Such fluoroscopic imaging system also includes an imaging management unit and a data storage unit, respectively connected to the imaging diagnostic apparatus.

The imaging management unit, generally called a Radiology Information System (hereinafter, RIS) or alike, serves to manage imaging order data used for picking up a fluoroscopic image data of the patient, in other words shooting a fluoroscopic image and thereby generating the fluoroscopic image data of the patient. The imaging order data include, for example, an imaging job identity (ID) which is exclusive identification data, identification data of the imaging diagnostic apparatus, identification data of the patient, date and time of the start and finish of the imaging. Meanwhile, the imaging order, also called an inspection order in actual medical sites.

The imaging order data is provided to the imaging diagnostic apparatus from the imaging management unit. The imaging diagnostic apparatus then picks up the fluoroscopic image data of the patient in correspondence with the imaging order data. The fluoroscopic image data is allocated with at least a part of the imaging order data in the imaging diagnostic apparatus, and output to the data storage unit.

The data storage unit, generally called a Picture Archive and Communication System (PACS) or alike, stores therein the fluoroscopic image data allocated with the imaging order data.

To the data storage unit, an image viewer, generally called a viewer, is connected. The image viewer reads out the fluoroscopic image data utilizing, for example, the imaging order data as the retrieval key, and displays that fluoroscopic image data.

It is to be noted that the imaging management unit is usually engaged in managing a plurality of imaging order data. Accordingly, one of the plurality of imaging order data managed by the imaging management unit has to be selectively provided to the imaging diagnostic apparatus. For this purpose, the imaging management unit is designed either as a push-type or as a pull-type.

The push-type imaging management unit selects one of the plurality of imaging order data under the management, for example through manual operation by the operator. The push-type imaging management unit transmits, upon receipt of a response request for the imaging order data from the imaging diagnostic apparatus, the selected one of the imaging order data, in response thereto.

To the pull-type imaging management unit, the imaging diagnostic apparatus transmits an order retrieval key with the response request for the imaging order data. The order retrieval key is composed of an imaging job ID for example, of the imaging order data.

Then the imaging management unit retrieves the imaging order data with the order retrieval key, and transmits the imaging order data thus retrieved as response to the imaging diagnostic apparatus. Upon receipt of the legitimate imaging order data, the imaging diagnostic apparatus picks up the fluoroscopic image data of the patient in correspondence with the imaging order data.

On the other hand, in the case where a plurality of imaging order data is retrieved and returned, the imaging diagnostic apparatus selects one of the plurality of imaging order data received, through manual operation by the operator for example.

In addition, once the imaging order data transmitted by the imaging management unit is fixed in the imaging diagnostic apparatus as above, such effect is notified to the imaging management unit. Accordingly, with the pull-type imaging management unit also, the imaging order data used for picking up the fluoroscopic image by the imaging diagnostic apparatus can be identified.

Regarding the foregoing fluoroscopic imaging system, various proposals have been made (for example, patent documents 1 and 2).

[Patent document 1] JP-A No. 2001-101320
[Patent document 2] JP-A No. 2005-198808.

DISCLOSURE OF THE INVENTION

Problem to be Solved by the Invention

In the foregoing fluoroscopic imaging system, the imaging diagnostic apparatus picks up the fluoroscopic image data of the patient, in other words shoots a fluoroscopic image thereby generating the fluoroscopic image data of the patient, in correspondence with the imaging order data, and the fluoroscopic image data is stored together with the imaging order data allocated thereto.

This makes it possible to retrieve the fluoroscopic image data with the imaging order data. Also, the imaging order data can be utilized for confirming the imaging condition and the like, when viewing the fluoroscopic image data.

However, despite that the patient who is to undergo the fluoroscopic image data pickup normally undergoes the injection of a medical liquid, also called a medical fluid, such as a contrast medium as already stated, the injection condition is not included in the imaging order data. Accordingly, it is impossible to confirm, upon viewing the fluoroscopic image data, how the liquid was injected into the patient.

The present invention has been accomplished in view of the foregoing problem, with an object to provide a fluoroscopic imaging system that allows an operator who views the fluoroscopic image data to confirm how a medical liquid (hereinafter simply liquid as the case may be) was injected into a patient when that fluoroscopic image data was picked up.

Means for Solving Problem

The present invention provides a fluoroscopic imaging system comprising an imaging diagnostic apparatus that picks up fluoroscopic image data of a patient; a liquid injector that injects a medical liquid into the patient who is to undergo the fluoroscopic image data pickup, and generates injection history data corresponding to the injection; a data control unit that allocates identification data associated with the fluoroscopic image data to the injection history data; and a data storage unit that stores therein the fluoroscopic image data and the injection history data in association with each other.

With the fluoroscopic imaging system thus constructed, the injection history data is also stored in association with the fluoroscopic image data to be stored, and therefore the injection history data can be confirmed when, for example, the fluoroscopic image data is viewed.

The present invention provides a first data control unit, being the data control unit of the fluoroscopic imaging system according to the present invention, that allocates identification data associated with the fluoroscopic image data to the injection history data. In the data control unit according to the present invention, therefore, the injection history data is associated with the fluoroscopic image data.

The present invention provides a second data control unit, being the data control unit of the fluoroscopic imaging system according to the present invention, comprising a history acquisition unit that acquires the injection history data from a liquid injector; an order acquisition unit that acquires, as the identification data, at least a part of the imaging order data corresponding to the injection history data, from at least one of the imaging management unit and the imaging diagnostic apparatus; an identification allocation unit that allocates the identification data to the injection history data; and a history transfer unit that outputs the injection history data allocated with the identification data to the data storage unit. In the data control unit according to the present invention, therefore, the injection history data is associated with the fluoroscopic image data.

The present invention provides a first liquid injector, being the liquid injector of the fluoroscopic imaging system according to the present invention, comprising a liquid injection mechanism that injects a medical liquid into the patient who is to undergo the fluoroscopic image data pickup; a history generation unit that generates the injection history data corresponding to the liquid injection; and a history output unit that outputs the generated injection history data to the data control unit. In the liquid injector according to the present invention, therefore, the injection history data associated with the fluoroscopic image data is output to the data control unit.

The present invention provides a second liquid injector, being the liquid injector of the fluoroscopic imaging system according to the present invention, comprising a liquid injection mechanism that injects a medical liquid into the patient whose fluoroscopic image data is to be picked up; an injection control unit that variably adjusts an injection rate of the liquid with the lapse of time; a history generation unit that generates injection history data including a time-based graph in which one of the horizontal axis and the vertical axis represents the lapse of time and the other the injection rate; and history output unit that outputs the generated injection history data to the data control unit. In the liquid injector according to the present invention, therefore, the injection history data including the time-based graph of the injection rate and associated with the fluoroscopic image data is output to the data control unit.

The present invention provides an image viewer, being the image viewer of the fluoroscopic imaging system according to the present invention, comprising a data readout unit that reads out from the data storage unit the fluoroscopic image data and the injection data associated with each other by the history data identification data; and a data display unit that displays the fluoroscopic image data and the injection history data that have been read out. The image viewer according to the present invention displays, therefore, the fluoroscopic image data together with the injection history data.

It is to be noted that each constituent of the present invention has only to be capable of performing its function, and may be constituted in a form of, for example, an exclusive hardware that performs a predetermined function, a data processor in which a predetermined function is incorporated as a computer program, a predetermined function realized in a data processor by a computer program, and an optional combination thereof.

Also, the constituents of the present invention do not necessarily have to be individually independent, but may be configured such that a plurality of constituents constitutes a single member, a constituent is composed of a plurality of members, a constituent is a part of another constituent, a part of a constituent and a part of another constituent overlap, and so forth.

Effect of the Invention

The fluoroscopic imaging system according to the present invention stores the injection history data in association with the fluoroscopic image data to be stored, to thereby allow confirming the injection history data at a time upon viewing the fluoroscopic image data, thus enabling the operator who views the fluoroscopic image data to even confirm how the medical liquid was injected into the patient when that fluoroscopic image data was picked up.

In the data control unit according to the present invention, the injection history data is associated with the fluoroscopic image data, which enables viewing also the injection history data when the fluoroscopic image data is read out to be viewed.

With the liquid injector according to the present invention, the injection history data associated with the fluoroscopic image data is output to the data control unit, and hence the injection history data associated with the fluoroscopic image data can be provided to the data control unit.

The image viewer according to the present invention displays also the injection history data when displaying the fluoroscopic image data, thereby enabling the operator who views the fluoroscopic image data to even confirm how the medical liquid was injected into the patient when that fluoroscopic image data was picked up.

BRIEF DESCRIPTION OF THE DRAWINGS

The above and other objects, features and advantages will become more apparent through a preferred embodiment described hereunder and the following accompanying drawings.

BEST MODE FOR CARRYING OUT THE INVENTION

Figure 1:
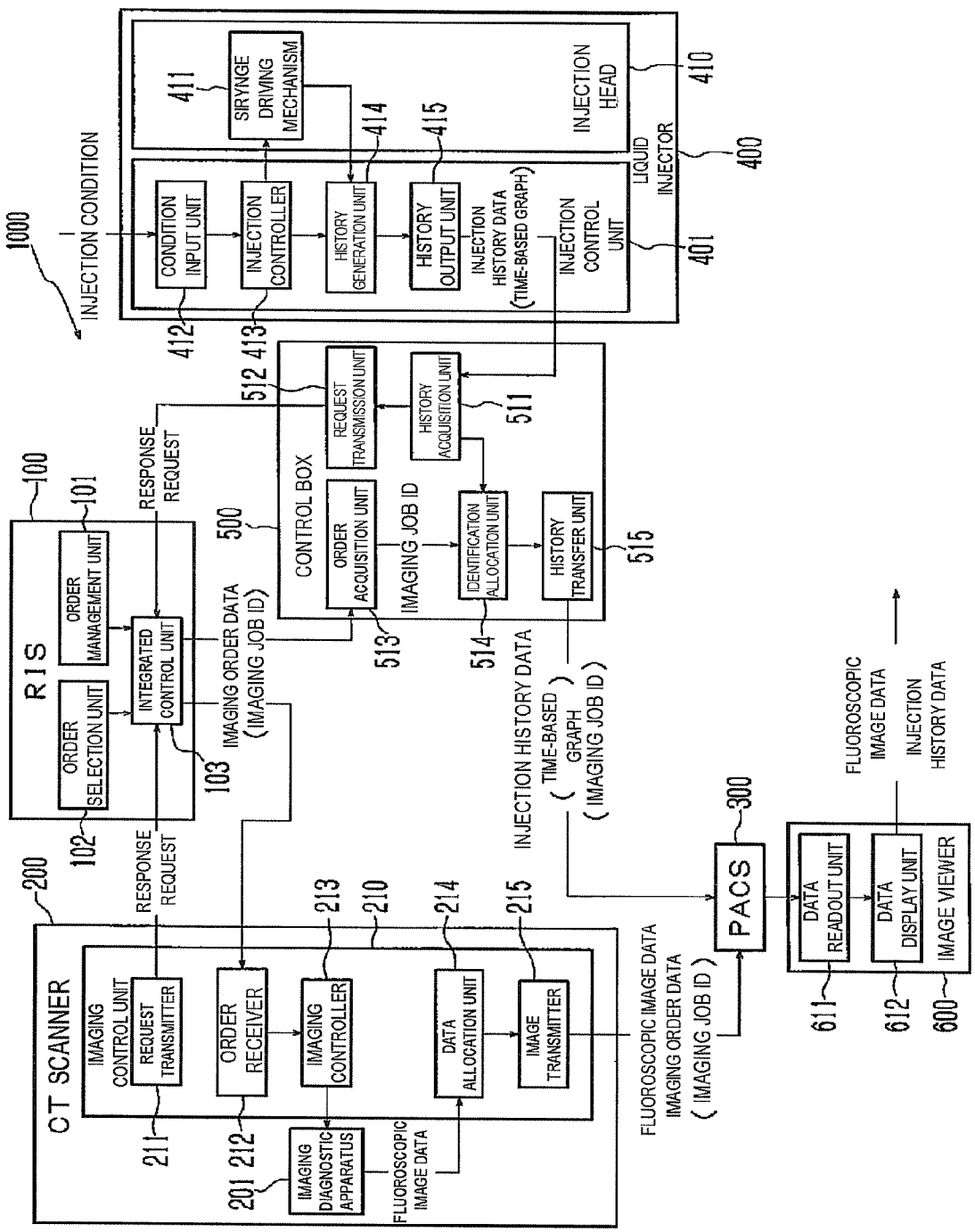
FIG. 1 is a schematic block diagram showing a logical structure of a fluoroscopic imaging system according to an embodiment of the present invention.
Figure 2:
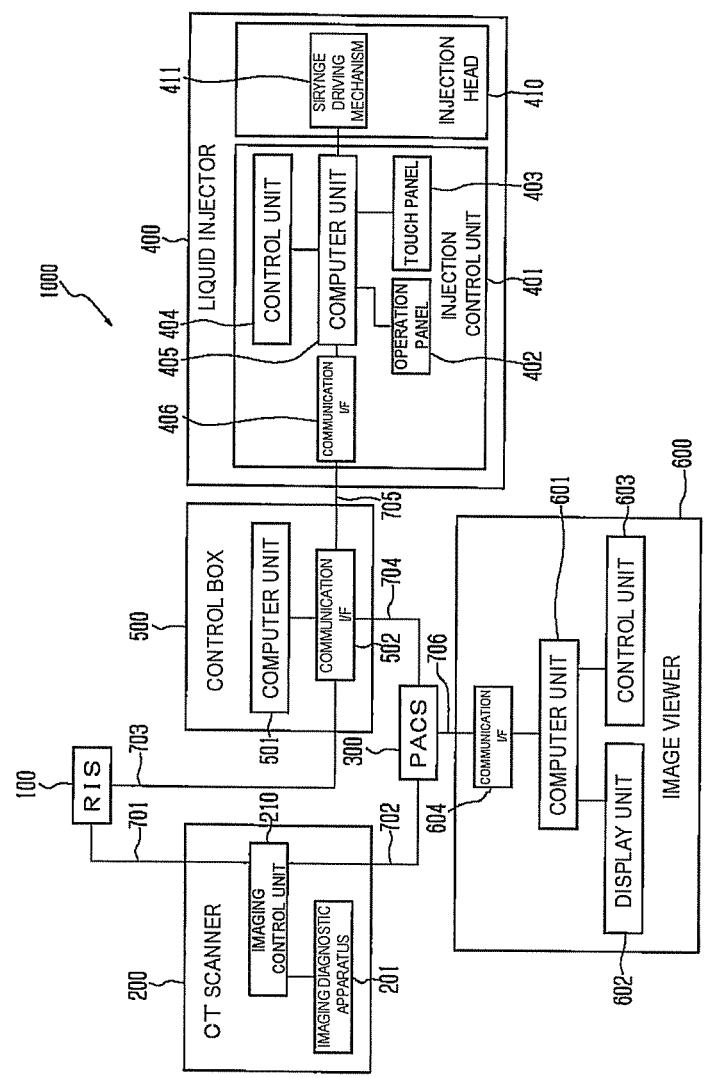
FIG. 2 is a block diagram showing a physical structure of the fluoroscopic imaging system.

Hereunder, an embodiment of the present invention will be described referring to the drawings. A fluoroscopic imaging system 1000 according to the embodiment of the present invention includes, as shown in FIGS. 1 and 2, a RIS 100 which serves as an imaging management unit, a CT scanner 200 which serves as an imaging diagnostic apparatus, a PACS 300 which serves as a data storage unit, a liquid injector 400, a control box 500 which serves as a data control unit, and an image viewer 600.

In the fluoroscopic imaging system 1000 according to this embodiment, the CT scanner 200 is connected to the RIS 100 and the PACS 300, through communication networks 701, 702 such as a Local Area Network (LAN), as illustrated.

The control box 500 is also connected to the RIS 100, the PACS 300, and the liquid injector 400 through communication networks 703 to 705. To the PACS 300, the image viewer 600 is connected through the communication network 706.

The fluoroscopic imaging system 1000 according to this embodiment is based on what is known as Digital Imaging and Communications in Medicine (DICOM). Accordingly, the respective units 100 to 600 of the fluoroscopic imaging system 1000 mutually communicate according to DICOM specification.

In the fluoroscopic imaging system 1000 according to this embodiment, one each of the CT scanner 200, the PACS 300, the liquid injector 400, and the control box 500 are provided, and all the combinations of these units are on a one-to-one basis.

The RIS 100 according to this embodiment is constituted of a known computer unit, in which an exclusive computer program is installed. In the RIS 100, an order management unit 101, an order selection unit 102, and an integrated control unit 103 are logically realized as the functions thereof, when the computer unit executes the corresponding processes according to the computer program.

The order management unit 101 corresponds to a storage device such as a hard disc drive (HDD), and serves to manage the imaging order data used for picking up fluoroscopic image data of the patient, in other words shooting a fluoroscopic image and thereby generating the fluoroscopic image data of the patient, with the exclusive identification data.

The imaging order data includes text data such as an imaging job ID which is the exclusive identification data, the identification data of the CT scanner 200, the identification data of the patient, and date and time of the start and finish of the imaging.

The order selection unit 102 corresponds to a function assigned to the central processing unit (hereinafter, CPU), including executing a predetermined process according to an input through a keyboard, and selects one from a plurality of imaging order data according to the input by the operator.

The integrated control unit 103 corresponds to a function assigned to the CPU including transmitting and receiving various data through a communication interface (I/F), and returns the selected one of the imaging order data according to a response request received from the CT scanner 200 or the control box 500.

The CT scanner 200 according to this embodiment includes, as shown in FIG. 2, a fluoroscopic imaging unit 201 which is the image-pickup execution mechanism, and an imaging control unit 210. The fluoroscopic imaging unit 201 shoots the fluoroscopic image data of the patient. The imaging control unit 210 controls the action of the fluoroscopic imaging unit 201.

To be more detailed, the imaging control unit 210 is constituted of a computer unit, in which an exclusive computer program is installed. In the imaging control unit 210, a request transmitter 211, an order receiver 212, an imaging controller 213, a data allocation unit 214, and an image transmitter 215 are logically realized as the functions thereof, when the computer unit executes the corresponding process according to the computer program.

The request transmitter 211 corresponds to a function assigned to the CPU including transmitting and receiving various data through the communication interface (I/F), and transmits the response request for the imaging order data to the RIS 100. The order receiver 212 receives the imaging order data returned from the RIS 100.

The imaging controller 213 controls the action of the fluoroscopic imaging unit 201 according to the imaging order data received. The data allocation unit 214 allocates the imaging order data to the fluoroscopic image data picked up by the fluoroscopic imaging unit 201.

The image transmitter 215 transmits the fluoroscopic image data allocated with the imaging order data to the PACS 300. Here, the fluoroscopic image data thus generated is composed of, for example, bit map data of the tomographic image.

The PACS 300 according to this embodiment is constituted of a database server, in which also an exclusive computer program is installed. The PACS 300 receives the fluoroscopic image data allocated with the imaging order data from the CT scanner 200, and stores the received data.

Figure 4:
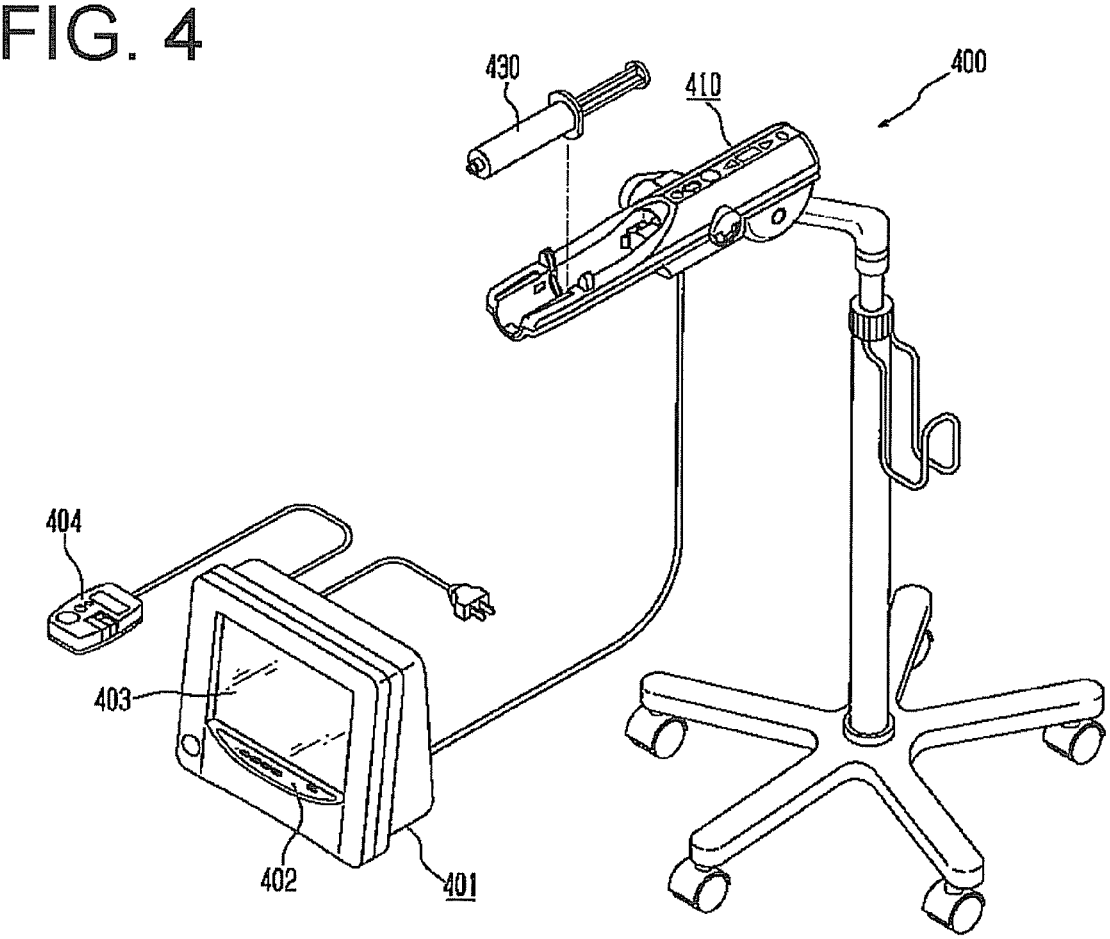
FIG. 4 is a perspective view showing the appearance of the liquid injector.
Figure 5:
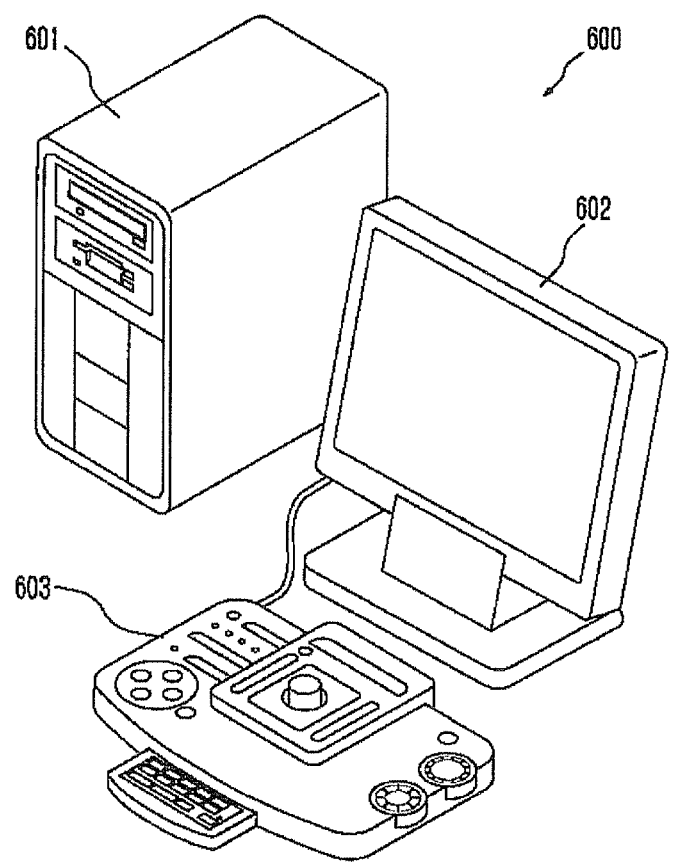
FIG. 5 is a perspective view showing an appearance of an image viewer.

The liquid injector 400 according to this embodiment includes, as shown in FIG. 4, an injection control unit 401 and an injection head 410. The injection control unit 401 controls the action of the injection head 410. The injection head 410 drives a liquid syringe 430 removably attached thereto, so as to inject a medical liquid (or simply liquid as the case may be), also called a medical fluid, into the patient.

To be more detailed, the injection control unit 401 includes, as shown in FIG. 2, an operation panel 402, a touch panel 403, a controller 404, a computer unit 405, a communication I/F 406. The injection head 410 includes a syringe driving mechanism 411, which is the liquid injection mechanism that drives the liquid syringe 430.

To the computer unit 405 of the liquid injector 400, the respective units cited above are connected. The computer unit 405 integrally controls the computer program, in which the respective units connected to the computer unit 405 are implemented.

Accordingly, in the liquid injector 400 according to this embodiment, units such as a condition input unit 412, an injection control unit 413, a history generation unit 414, and a history output unit 415, are logically realized as the functions thereof, as shown in FIG. 1.

The condition input unit 412 corresponds to a function assigned to the computer unit 405, including detecting an input made through the operation panel 402 and the touch panel 403 according to the computer program, and accepts an input of the injection condition. The injection condition thus input includes identification data of the liquid, identification data of the region to be imaged, a target graph for variably adjusting the injection rate of the contrast medium, which is a medical liquid.

The injection control unit 413 corresponds to a function assigned to the computer unit 405, including controlling the action of the syringe driving mechanism 411 according to the computer program and the data input to the operation panel 402, and variably adjusts the injection rate of the liquid from the syringe driving mechanism 411 with the lapse of time, according to the injection condition that has been input.

The history generation unit 414 corresponds to a function assigned to the computer unit 405, including executing a predetermined process according to the computer program, and generates the injection history data corresponding to the liquid injection.

The injection history data this generated includes text data such as an injection job ID which is exclusive identification data of each injection job, date and time of the start and finish of the injection, identification data of the liquid injector 400, and identification data of the liquid and the region to be imaged, which constitute the injection condition, and image data of the time-based graph in which one of the horizontal axis and the vertical axis represents the lapse of time and the other the injection rate.

The history output unit 415 corresponds to a function assigned to the computer unit 405 including executing data communication through the communication I/F 406, and transmits the generated injection history data to the control box 500.

The control box 500 according to this embodiment includes, as shown in FIG. 2, a computer unit 501 in which an exclusive computer program is installed, and a communication I/F 502.

In the control box 500, as shown in FIG. 1, units such as a history acquisition unit 511, a request transmission unit 512, an order acquisition unit 513, an identification allocation unit 514, and a history transfer unit 515, are logically realized as the function thereof, to be performed when the computer unit 501 executes the corresponding process according to the computer program.

The history acquisition unit 511 corresponds to a function assigned to the computer unit 501 including accepting reception data through the communication I/F 502, according to the computer program, and receives the injection history data from the liquid injector 400.

The request transmission unit 512 corresponds to a function assigned to the computer unit 501 including causing the communication I/F 502 to transmit the data according to the computer program, and transmits the response request for the imaging order data to the RIS 100 upon receipt of the injection history data.

The order acquisition unit 513 also corresponds to a function assigned to the computer unit 501 including accepting the reception data through the communication I/F 502, and receives the imaging order data the returned from the RIS 100.

The identification allocation unit 514 corresponds to a function assigned to the computer unit 501 including executing a predetermined process, and allocates the imaging job ID, the identification data exclusive to the imaging order data, to the injection history data.

The history transfer unit 515 corresponds to a function assigned to the computer unit 501 including causing the communication I/F 502 to transmit the data, and outputs the injection history data allocated with the imaging job ID, to the PACS 300.

Thus, the PACS 300 according to this embodiment stores not only the foregoing fluoroscopic image data received from the CT scanner 200, but also the injection history data received from the control box 500 as above.

As stated earlier, the fluoroscopic image data is allocated with the imaging order data, and the imaging job ID of the imaging order data is allocated to the injection history data. Accordingly, the imaging order data and the injection history data are mutually associated via the imaging job ID, when stored in the PACS 300.

The image viewer 600 according to this embodiment also includes a computer unit in which an exclusive computer program is installed. The image viewer 600 includes a computer unit 601, a display unit 602, a controller 603, a communication I/F 604, and so on.

In the image viewer 600 includes, as shown in FIG. 1, a data readout unit 611 and a data display unit 612, to be performed when the computer unit 601 executes the corresponding process according to the computer program.

The data readout unit 611 corresponds to a function assigned to the computer unit 601 including making access to the PACS 300 through the communication I/F 604 according to the computer program and the data input to the controller 603, and reads out the fluoroscopic image data and the injection history data imaging mutually associated via the job ID, from the PACS 300.

The data display unit 612 corresponds to the function assigned to the computer unit 601 including causing the display unit 602 to display the data received through the communication I/F 604, and displays the fluoroscopic image data and the injection history data that have been read out.

It is to be noted that the foregoing computer programs of the RIS 100 are described as software for causing the RIS 100 to, for example, manage the imaging order data for picking up the fluoroscopic image data of the patient with the exclusive identification data, select one from a plurality of imaging order data according to an input by an operator, return the selected imaging order data according to the response request from the CT scanner 200 or the control box 500, and so forth.

The computer program of the CT scanner 200 is described as software for causing the imaging control unit 210 to, for example, transmit the response request for the imaging order data to the RIS 100 according to an input by the operator, receive the imaging order data returned from the RIS 100, control the action of the fluoroscopic imaging unit 201 according to the imaging order data that has been received, allocate the fluoroscopic image data picked up by the fluoroscopic imaging unit 201 with the imaging order data, and transmit the fluoroscopic image data allocated with the imaging order data to the PACS 300.

The computer program of the liquid injector 400 is described as software for causing the computer unit 405 to, for example, accept the input of the injection condition, variably adjust the injection rate of the liquid by the syringe driving mechanism 411 according to the injection condition that has been input, generate the injection history data including the time-based graph corresponding to the liquid injection, and transmit the generated injection history data to the control box 500.

The computer program of the control box 500 is described as software for causing the computer unit 501 to, for example, receive the injection history data from the liquid injector 400, transmit the response request for the imaging order data to the RIS 100 upon receipt of the injection history data, receive the imaging order data returned from the RIS 100, allocate the imaging job ID, which is the exclusive identification data of the imaging order data, to the injection history data, and output the injection history data allocated with the imaging job ID to the PACS 300.

The computer program of the PACS 300 is described as software for causing the PACS 300 to, for example, receive the fluoroscopic image data allocated with the imaging order data from the CT scanner 200 and store the fluoroscopic image data, and receive the injection history data allocated with the imaging job ID of the imaging order data from the control box 500, and store the injection history data.

The computer program of the image viewer 600 is described as software for causing the computer unit 601 to, for example, read out the fluoroscopic image data and the injection history data mutually associated via the imaging job ID from the PACS 300, and display the fluoroscopic image data and the injection history data that have been read out.

Hereunder, a procedure of picking up the fluoroscopic image data of the patient with the fluoroscopic imaging system 1000 thus configured according to this embodiment will be sequentially described. To start with, the operator registers in advance the imaging order data in the RIS 100. Accordingly, the operator engaged in executing the imaging job can select one of the imaging order data corresponding to the ongoing imaging job, by manually operating the RIS 100.

The imaging order data is composed of the text data including the imaging job ID, the identification data of the CT scanner 200, the identification data of the patient, and date and time of the start and finish of the imaging. In other words, the imaging order data includes those data necessary for the CT scanner 200 to execute the imaging job, but does not include the data that enables identifying the injection job of the liquid injector 400.

Figure 3:
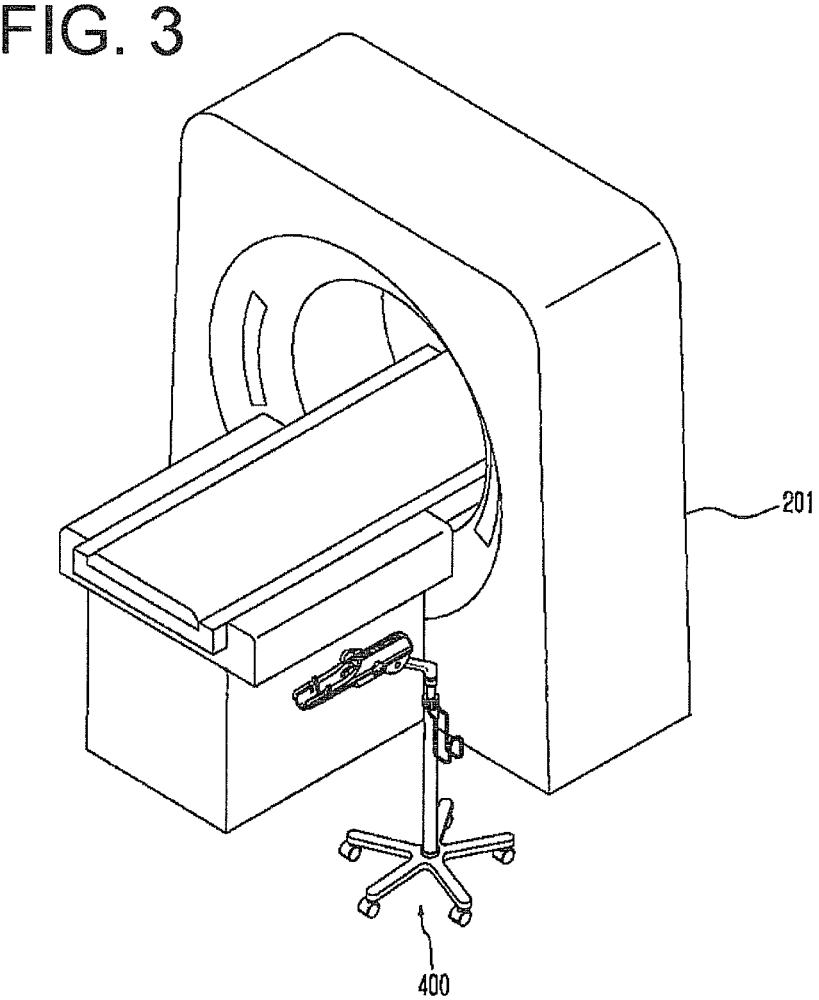
FIG. 3 is a perspective view showing an appearance of a fluoroscopic imaging unit of a CT scanner and an injection head of a liquid injector.

Meanwhile at the actual site of the imaging job, the liquid injector 400 is located close to the fluoroscopic imaging unit 201 of the CT scanner 200, as shown in FIG. 3. Then the liquid syringe 430 is connected to the patient in the imaging unit 301 (not shown) through an extension tube, and the liquid syringe 430 is loaded onto the injection head 410 of the liquid injector 400.

Figure 6:
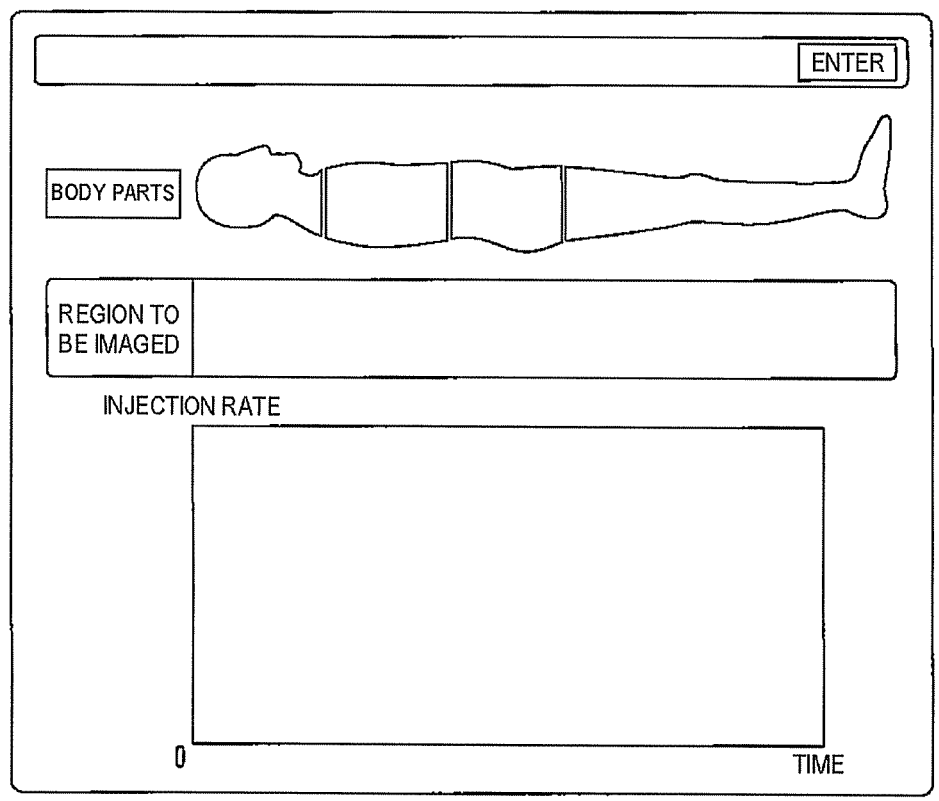
FIG. 6 is a schematic front view showing a screen of the liquid injector, displaying a simulated image of body parts and condition columns in blank.

Once the operator activates the liquid injector 400 for example by an inputting action through the operation panel 402 of the injection control unit 401, a simulated image of a plurality of body parts is displayed in an upper portion of the touch panel 403, as shown in FIG. 6.

Below the simulated image, a selection screen of the region to be imaged is displayed, in a horizontally slender rectangular shape. In a lower portion of the touch panel 403, a horizontally stretched rectangular-shaped condition screen is displayed, a vertical axis of which represents the injection rate of the liquid, and a horizontal axis the injection time. Under such state, the operator inputs, for example, the identification data of the liquid and that of the region to be imaged through the operation panel 402, as a part of the injection condition.

Figure 7:
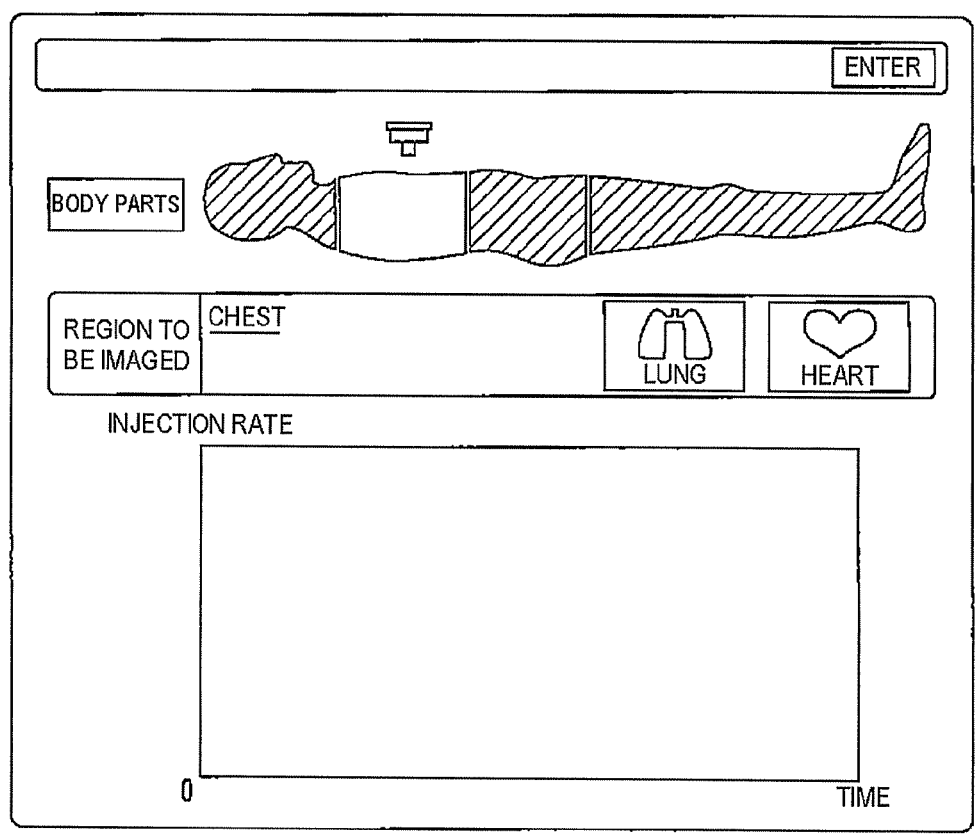
FIG. 7 is a schematic front view showing the screen of the liquid injector, displaying a state where a body part has been selected.

The operator then presses with a finger one of the plurality of body parts of the simulated image displayed on the touch panel 403. Then only the selected part of the simulated image is lit up while all the remaining parts are turned off, as shown in FIG. 7, and an icon of the scanner mechanism is displayed above the selected part of the simulated image.

Figure 8:
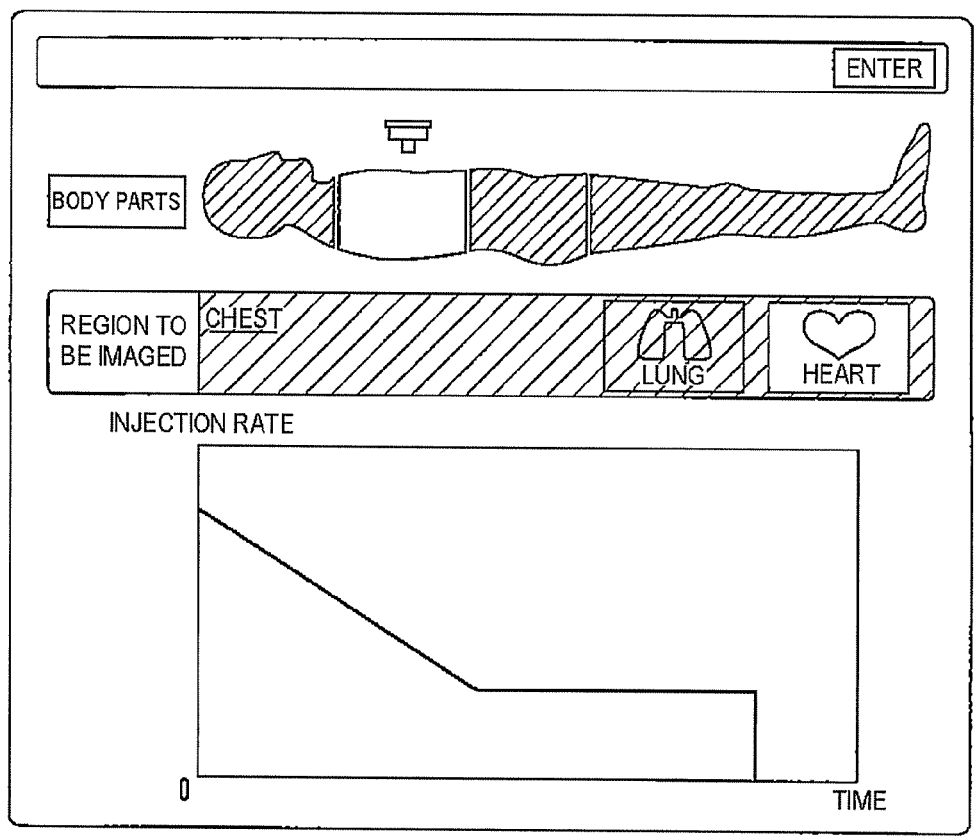
FIG. 8 is a schematic front view showing the screen of the liquid injector, displaying the selected region to be imaged and a target graph.

At the same time, below the selected part, icons of a plurality of regions to be imaged corresponding to the selected body part is read out and displayed in the selection screen. When the operator inputs one of the icons by pressing with a finger, only the selected icon is lit up and the others are turned out, as shown in FIG. 8.

Once the region to be imaged is thus selected, the target graph corresponding to the region to be imaged is read out and set as the injection condition by the computer unit 405, in the liquid injector 400 of this embodiment.

The target graph is then displayed as the target to be followed up, in the condition screen on the touch panel 403. Once the start of the injection is input under such state, the liquid injector 400 controls, upon detecting the input, the action of the syringe driving mechanism 411 according to the target graph to be followed, to thereby inject the contrast medium into the patient.

In this process, the lapse of time is measured on a real time basis and the actual injection rate is detected, so that a feedback control is executed upon the syringe driving mechanism 411 such that the injection rate agrees with the target graph.

Figure 9:
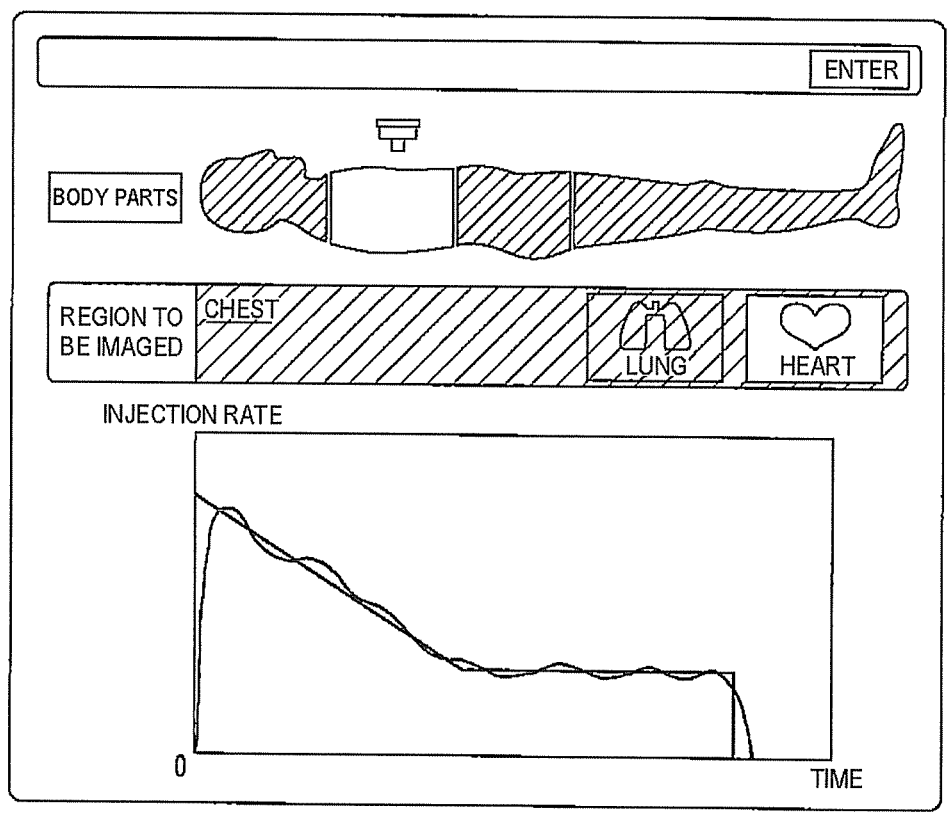
FIG. 9 is a schematic front view showing the screen of the liquid injector, displaying the target graph and a time-based graph.

Also, the time-based graph indicating the actual injection rate is generated on a real time basis, and is displayed with the target graph on the touch panel 403 as shown in FIG. 9. When the injection job is completed, the injection history data including the time-based graph corresponding to the actual injection rate is generated.

The injection history data thus generated is composed of the text data including the injection job ID, the date and time of the injection job, the identification data of the liquid injector 400, that of the liquid, and that of the region to be imaged, and the image data of the foregoing time-based graph. In other words, the injection history data includes those data necessary for confirming the details of the injection job executed by the, but does not include the data that enables identifying the imaging order data.

Upon completing the injection job, the liquid injector 400 transmits the generated imaging order data to the control box 500. The control box 500 transmits, upon receipt of the imaging order data from the liquid injector 400, the response request for the imaging order data to the RIS 100.

The RIS 100 then returns the imaging order data selected as already described to the control box 500. The control box 500 extracts, upon receipt of the imaging order data from the RIS 100, the imaging job ID of the imaging order data and allocates such ID to the injection history data.

Then the control box 500 transmits the injection history data allocated with the imaging job ID to the PACS 300. The PACS 300 stores the received injection history data, utilizing the imaging job ID as the index.

Meanwhile, in a normal operation, around the time when the liquid injector 400 completes the injection job as above, the imaging job by the CT scanner 200 is started. In this case, the operator inputs the start of the imaging job to the imaging control unit 210 of the CT scanner 200.

The imaging control unit 210 of the CT scanner 200 then transmits the response request for the imaging order data to the RIS 100. The RIS 100 returns the imaging order data selected as above to the CT scanner 200.

The CT scanner 200 controls the action of the fluoroscopic imaging unit 201 according to the imaging order data received by the imaging control unit 210, so that the fluoroscopic image executes the imaging job.

Thereafter, once the fluoroscopic imaging unit 201 shoots the fluoroscopic image data of the patient, the imaging control unit 210 allocates the fluoroscopic image data with the imaging order data. The imaging control unit 210 then transmits the fluoroscopic image data allocated with the imaging order data to the PACS 300.

The PACS 300 stores the fluoroscopic image data, utilizing the imaging job ID of the imaging order data as the index. When the operator is to review the fluoroscopic image data, the operator may manually operate, for example, the image viewer 600, to thereby read out the fluoroscopic image data from the PACS 300.

In this case, inputting for example the imaging job ID as the retrieval key causes the fluoroscopic image data corresponding to that imaging job ID to be read out from the PACS 300, and to be displayed on the display unit 602 of the image viewer 600. At this moment the injection history data is also read out from the PACS 300 with the same imaging job ID, and can be displayed on the display unit 602 of the image viewer 600, if need be.

The fluoroscopic imaging system 1000 according to this embodiment stores the injection history data in association with the fluoroscopic image data as stated above, thereby allowing confirming the injection history data, for example upon reviewing the fluoroscopic image data. Accordingly, the operator who reviews the fluoroscopic image data can also confirm how the liquid was injected into the patient when that fluoroscopic image data was picked up.

In particular, in the fluoroscopic imaging system 1000 according to this embodiment, the liquid injector 400 variably adjusts the injection rate of the contrast medium in order to upgrade the quality of the fluoroscopic image data to be picked up by the CT scanner 200. Also, since the time-based graph corresponding to the injection rate is included in the injection history data, the injection process of the contrast medium can be confirmed in details.

In the case where the injection job of the contrast medium turns to be suspicious, the injection history data can be employed as the evidence, because the injection history data can also be confirmed together with the fluoroscopic image data.

In particular, the units 100 to 600 of the fluoroscopic imaging system 1000 according to this embodiment mutually execute the data communication in accordance with the DICOM standards. Since it is difficult to falsify the communication data according to DICOM, the injection history data has high admissibility as evidence.

Also, in the case of picking up the fluoroscopic image data of the same patient again, the previous injection history data can be referred to. Accordingly, the appropriate injection condition can be easily input into the liquid injector 400.

In the case of picking up the fluoroscopic image data again, particularly from a patient whose weight has been fluctuating because of the progress of the disease, reviewing the previous fluoroscopic image data and the injection history data allows simply inputting the appropriate injection condition into the liquid injector 400.

Also, in this embodiment the injection history data includes the time-based graph. Accordingly, even though the injection condition is so complicated as to correct the target graph along which the injection rate is to be variably adjusted, the injection condition can be simply input into the liquid injector 400.

Further, in the fluoroscopic imaging system 1000 according to this embodiment, the injection history data including the text data such as the injection condition is stored in the PACS 300. Such arrangement allows generating, for example, various statistical data related to the liquid injection, from the numerous injection history data accumulated in the PACS 300.

Particularly, since the injection history data is stored together with the imaging order data and so on, various statistical data related to the liquid injection can be generated together with the imaging condition and so on included in the imaging order data.

Here, in the fluoroscopic imaging system 1000 according to this embodiment, the imaging order data and the fluoroscopic image data do not include, as in the conventional system, those data that allows identifying the injection condition input to the liquid injector 400 and the generated injection history data.

Likewise, the injection condition input to the liquid injector 400 and the generated injection history data do not include either, those data that permits identifying the imaging order data and the fluoroscopic image data. In other words, the imaging order data cannot be identified from the injection history data, as in the conventional system.

Normally, however, the imaging job by the CT scanner 200 is started around the time when the liquid injector 400 completes the injection job. Also, by the time that the CT scanner 200 starts the imaging job, one imaging order data is selected in the RIS 100.

Accordingly, in consideration of such situation, in the fluoroscopic imaging system 1000 according to this embodiment, the control box 500 acquires the imaging order data at the time when the injection history data is input. Such arrangement allows the control box 500 to acquire the proper without executing data retrieval or data look-up, so as to allocate the imaging order data to the injection history data.

Further, in the fluoroscopic imaging system 1000 according to this embodiment, the control box 500 only extracts the imaging job ID from the imaging order data, and allocates such ID to the injection history data. Such arrangement assures the association of the injection history data with the fluoroscopic image data, with a minimal necessary data capacity.

It is to be noted that the present invention is not in any way limited to the foregoing embodiment, but allows various modifications within the scope of the present invention. For example, the above embodiment represents the case where the fluoroscopic imaging system 1000 includes one each of the respective units, for the sake of explicitness of the description.

However, in a large-scaled hospital or the like, each of a plurality of fluoroscopic imaging systems may include one each of the RIS 100, the CT scanner 200, the liquid injector 400, and the control box 500, and the plurality of fluoroscopic imaging systems may share the PACS 300 and the image viewer 600 (not shown). In such case also, the hardware such as the RIS 100, the PACS 300, and the image viewer 600 may be prepared in a plurality of numbers and connected in parallel (not shown).

Also, the foregoing embodiment represents the case where the fluoroscopic image data and the injection history data are stored in a single unit of the PACS 300. However, the hardware that stores the fluoroscopic image data and the hardware that stores the injection history data may be independently prepared and connected via the communication network.

The foregoing embodiment represents the case where the RIS 100, the CT scanner 200, the PACS 300, the liquid injector 400, the control box 500, and the image viewer 600 are separately formed and mutually connected via the communication network 701 to 706.

However, the respective units 200 to 600 may be integrally constituted in various combinations. To cite a few examples, the injection control unit 401 of the liquid injector 400 and the control box 500 may be integrally constituted; the RIS 100 and the PACS 300 may be added to such combination to thereby form a unified structure; and the PACS 300 and the image viewer 600 may be integrally constituted.

Also, the control box 500 may be unified with the RIS 100 and the PACS 300, and the control box 500, the PACS 30, and the image viewer 600 may be integrally constituted.

Further, the imaging control unit 210 of the CT scanner 200, the RIS 100, and the control box 500 may be integrally constituted; the imaging control unit 210 of the CT scanner 200, the PACS 300, and the control box 500 may be integrally constituted; and the image viewer 600 may be added to thereby form a unified structure.

Further, the image viewer 600 and the PACS 300 may be integrally constituted; and the control box 500, and the imaging control unit 210 of the CT scanner 200 may be added to thereby form a unified structure.

The foregoing embodiment represents the case where the entirety of the imaging order data is allocated to the fluoroscopic image data, and stored in the PACS 300. However, only the imaging job ID may be allocated to the fluoroscopic image data, from the imaging order data.

In this case also, the fluoroscopic image data and the injection history data can be mutually associated via the imaging job ID, and the imaging order data can be read out from the RIS 100 with the imaging job ID.

Also, only the imaging job ID out of the imaging order data may be allocated to the fluoroscopic image data, while allocating the entirety of the imaging order data to the injection history data, and the imaging order data may be dividedly allocated to the fluoroscopic image data and the injection history data.

Further, the injection history data may include both of the time-based graph and the target graph. The entire display content on the touch panel 403 of the liquid injector 400 may be included in the injection history data.

The foregoing embodiment represents the case where the injection history data is composed of the text data including the injection job ID, date and time and so on, and the image data including the time-based graph of the injection rate. However, the injection history data may only contain the text data.

In particular, the foregoing embodiment represents the case where the liquid injector 400 variably adjusts the injection rate of the contrast medium, and stores the corresponding time-based graph as a part of the injection history data. However, the liquid injector 400 may inject the contrast medium at a constant rate. In this case, it barely makes sense to generate the time-based graph and store the same. Accordingly, it is more preferable to include the injection rate in a form of the text data in the injection history data.

The foregoing embodiment represents the case where the control box 500 acquires the imaging order data from the RIS 100 upon receipt of the injection history data from the liquid injector 400. However, the liquid injector 400 may notify the control box 500 of the start and finish of the injection job, so that the control box 500 acquires the imaging order data from the RIS 100, upon receipt of such notice. Such arrangement allows the control box 500 to acquire the proper imaging order data, even in the case where the liquid injection and the fluoroscopic image pickup are executed at the same time.

Also, the control box 500 may acquire the imaging order data from the RIS 100 after a predetermined period of time from the receipt of the injection history data or the notice of the start or finish. Such arrangement allows the control box 500 to acquire the proper imaging order data, even though the imaging job of the fluoroscopic image is started after the predetermined period of time from the completion of the liquid injection job.

Likewise, the liquid injector 400 may notify the control box 500 of the start and finish of the liquid injection after the predetermined period of time, so that the control box 500 transmits the response request upon receipt of the notice from the liquid injector 400.

Further, the CT scanner 200 may notify the control box 500 of the start and finish of the imaging job, so that the control box 500 acquires the imaging order data from the RIS 100.

Further, the control box 500 may acquire the imaging order data from the RIS 100 after the predetermined period of time from the receipt of the imaging history data or the notice of the start and finish. Likewise, the CT scanner 200 may notify the control box 500 of the start and finish of the imaging of the liquid after the predetermined period of time, so that the control box 500 transmits the response request upon receipt of the notice from the CT scanner 200.

Still further, the control box 500 which has received the notice of the start and finish of the injection from the liquid injector 400 as above may notify the RIS 100 of such start and finish. Such arrangement allows the RIS 100 to notify the CT scanner 200 of the start time and the finish time of the liquid injection, together with the imaging order data and so on.

Accordingly, the operator handling the CT scanner 200 can refer to the start time and the finish time of the liquid injection, and hence the operator can adjust the start time of the image pickup, according to the time of the liquid injection.

Likewise, the liquid injector 400 may notify the control box 500 of the injection condition, and the injection condition may be notified to the RIS 100 by the control box 500. In this case, the injection condition can be notified to the CT scanner 200 from the RIS 100, together with the imaging order data and so on.

Such arrangement allows the operator handling the CT scanner 200 to refer to the injection condition, thereby facilitating the operator to adjust the imaging action according to the injection condition. It is also feasible to automatically control the imaging action based on the injection condition acquired by the imaging control unit 210 of the CT scanner 200.

The foregoing embodiment represents the case where the liquid injector 400 transmits the injection history data, upon completion thereof, to the control box 500. However, the liquid injector 400 may transmit the injection history data in separate portions to the control box 500, so that the control box 500 unifies the injection history data.

To be more detailed, the liquid injector 400 may transmit, upon starting the injection, the injection condition and the date and time of the start of the injection to the control box 500; sequentially transmit the injection rate and so on during the injection process; and transmit the finish time upon completing the injection. In this case, the control box 500 can complete the injection history data from various data accumulated during the injection process, and output the completed data.

The foregoing embodiment represents the case where the liquid injector 400 injects only the contrast medium into the patient with a single liquid syringe 430. However, the liquid injector may employ a plurality of liquid syringes so as to inject the contrast medium and physiological saline as the medical liquid or medical fluid, into the subject (not shown).

For example, in the case where the liquid injector is to sequentially inject the contrast medium and the physiological saline as the medical liquid into the patient, at least one of the finish of the injection of the contrast medium and the start of the injection of the physiological saline may be notified to the control box 500.

Alternatively, the liquid injector set to sequentially inject the contrast medium and the physiological saline as the medical liquid into the patient may transmit the injection history data of the contrast medium to the control box 500, upon completion of the injection of the contrast medium.

The foregoing embodiment represents the case where the RIS 100 is of the push-type, and the control box 500 acquires the proper imaging order data at a predetermined timing. However, the RIS 100 may be of the pull-type.

In the latter case, the CT scanner 200 transmits the response request for the imaging order data to the RIS 100 with at least an order retrieval key. Then the RIS 100 selects one of the plurality of imaging order data according to the response request and the order retrieval key received from the CT scanner 200, and returns the selected data.

The control box 500 then transmits the response request for the imaging order data to the RIS 100 at a predetermined timing corresponding to the liquid injection. The RIS 100 returns the selected imaging order data according to the response request received from the control box 500.

Alternatively, the RIS 100 may return a plurality of imaging order data according to the response request received from the CT scanner 200. In this case, the CT scanner 200 accepts an operation of selecting one of the plurality of imaging order data returned, and notifies the RIS 100 of the selected imaging order data.

The RIS 100 may also retrieve a part of the plurality of imaging order data based on the response request and the order retrieval key received from the CT scanner 200, and return the retrieved data. The CT scanner 200 accepts an operation of selecting one of the imaging order data returned, and notifies the RIS 100 of the selected imaging order data.

Once the control box 500 transmits the response request for the imaging order data to the RIS at a predetermined timing corresponding to the liquid injection, the RIS 100 returns the one of the imaging order data notified of by the CT scanner 200, according to the response request received from the control box 500.

Such arrangement allows the control box 500 to acquire the proper imaging order data despite that the RIS 100 is of the pull-type, and to allocate the imaging job ID and so on to the injection history data.

The foregoing embodiment represents the case where the control box 500 unconditionally acquires the imaging order data provided by the RIS 100. However, the control box 500 may transmit the response request for the imaging order data to the RIS 100 with at least an order retrieval key.

In this case, the RIS 100 retrieves a part of the plurality of imaging order data according to the order retrieval key received from the control box 500, and if the retrieved imaging order data includes the one notified of by the CT scanner 200, the RIS 100 returns that one. Such arrangement further assures that the control box 500 acquires the proper imaging order data.

Here, in the foregoing case, the liquid injector 400 may transmit the generated injection history data to the control box 500, so that the control box 500 may transmit at least a part of the received injection history data to the RIS 100, as the order retrieval key.

Such arrangement allows the control box 500 to generate the proper order retrieval key from the injection history data, and to thereby allocate the proper imaging order data to the injection history data.

The foregoing embodiment represents the case where the control box 500 acquires the imaging order data from the RIS 100. However, the RIS 100 and the CT scanner 200 may be connected via the control box 500, so that the control box 500 may acquire the imaging order data which is transmitted from the RIS 100 to the CT scanner 200.

Also, the control box 500 may be connected to the CT scanner 200 without being connected to the RIS 100, so as to acquire the imaging order data from the CT scanner 200. In this case, for example, the control box 500 may transmit the response request for the imaging order data to the CT scanner 200 at the predetermined timing corresponding to the liquid injection, and the CT scanner 200 may return the imaging order data according to the response request received from the control box 500.

Alternatively, the CT scanner 200 may transfer the imaging order data returned from the RIS 100 to the control box 500. Further, the CT scanner 200 may accept an operation of selecting one of the plurality of imaging order data returned from the pull-type RIS 100, to thereby transfer the selected imaging order data to the control box 500.

The foregoing embodiment represents the case where the CT scanner 200 serves as the imaging diagnostic apparatus, and the liquid injector 400 injects the contrast medium as the medical liquid, for CT scanning. However, a MRI equipment, a PET equipment, or an ultrasonic diagnostic equipment may be employed as the imaging diagnostic apparatus, and the liquid injector may inject the contrast medium prepared exclusively for such equipments.

Also, the foregoing embodiment represents the case where the CT scanner 200 and the liquid injector 400 are independently activated on a stand-alone basis. However, the CT scanner 200 and the liquid injector 400 may work in correlation to perform various actions, through data communication.

Further, the foregoing embodiment represents the case where the respective units 100 to 600 mutually perform the data communication according to DICOM standards which is difficult to falsify, thereby securing high admissibility of the injection history data as evidence. However, the liquid injector 400 may generate the injection history data in a data format difficult to falsify, such as the Portable Document Format (PDF).

Likewise, the control box 500 may convert the injection history data received from the liquid injector 400 in the Joint Photographic Coding Experts Group (JPEG) format into the PDF format. Further, the liquid injector 400 and the control box 500 may be connected to what is known as the Internet, so as to acquire an electronic signature and allocate the injection history data with the same.

Still further, the foregoing embodiment represents the case where the computer unit works according to the computer program, to thereby logically realize the respective units 100 to 600 to perform the assigned functions. However, it is also possible to set up the respective units as individually independent hardware, or some units as hardware and the others as software.

Naturally, the foregoing structures may be combined in various manners, unless contradiction is incurred.

The invention claimed is:
1. A fluoroscopic imaging system, comprising:
an imaging diagnostic apparatus that picks up fluoroscopic image data of a patient;
a liquid injector that is adapted to inject a medical liquid into said patient whose fluoroscopic image data is to be picked up, and generates injection history data that show specific process information of said injection;

a first computer that allocates identification data associated with said fluoroscopic image data to said injection history data; and a database server that stores therein said fluoroscopic image data and said injection history data in association with each other, wherein after the liquid injector completes the injection of the medical liquid into said patient, the liquid injector generates the injection history data and transmits the injection history data to the first computer;

after the first computer receives the injection history data from the liquid injector, the first computer receives imaging order data from a second computer or the imaging diagnostic apparatus, extracts an imaging job identity from the imaging order data, and attaches the imaging job identity to the injection history data; and the database server stores the injection history data that is attached with the imaging job identity together with the fluoroscopic image data that is attached with at least a part of the imaging order data, the part of the imaging order data comprising the imaging job identity.

2. The fluoroscopic imaging system according to claim 1, wherein the second computer manages imaging order data used for causing said imaging diagnostic apparatus to pick up said fluoroscopic image data;

said imaging diagnostic apparatus picks up said fluoroscopic image data of said patient according to said imaging order data;

said database server stores said fluoroscopic image data allocated with at least a part of said imaging order data; and said first computer acquires, as said identification data, at least a part of said imaging order data corresponding to said injection history data, from at least one of said second computer and said imaging diagnostic apparatus.

3. The fluoroscopic imaging system according to claim 2, wherein said imaging diagnostic apparatus and said first computer are connected to said second computer via a communication network;

said second computer manages a plurality of said imaging order data;

said imaging diagnostic apparatus transmits a response request for said imaging order data to said second computer with at least one order retrieval key;

said second computer selects and returns one of said plurality of imaging order data according to said response request received from said imaging diagnostic apparatus and said order retrieval key;

said first computer transmits said response request for said imaging order data to said second computer at a predetermined timing corresponding to said injection of said medical liquid; and said second computer returns said one of said imaging order data according to said response request received from said first computer.

4. The fluoroscopic imaging system according to claim 2, wherein said imaging diagnostic apparatus and said first computer are connected to said second computer via a communication network;

said second computer manages a plurality of said imaging order data;

said imaging diagnostic apparatus transmits a response request for said imaging order data to said second computer with at least one order retrieval key;

said second computer retrieves and returns a part of said plurality of imaging order data according to said response request received from said imaging diagnostic apparatus and said order retrieval key;

said imaging diagnostic apparatus accepts an operation of selecting one of said imaging order data returned, and notifies said second computer of said one selected from said imaging order data;

said first computer transmits said response request for said imaging order data to said second computer at a predetermined timing corresponding to said injection of said medical liquid; and said second computer returns said one of said imaging order data notified of by said imaging diagnostic apparatus according to said response request received from said first computer.

5. The fluoroscopic imaging system according to claim 2, wherein said imaging diagnostic apparatus and said first computer are connected to said second computer via a communication network;

said second computer manages a plurality of said imaging order data;

said imaging diagnostic apparatus transmits a response request for said imaging order data to said second computer with at least one order retrieval key;

said second computer selects and returns one of said plurality of imaging order data according to said response request received from said imaging diagnostic apparatus and said order retrieval key;

said first computer transmits said response request for said imaging order data to said imaging diagnostic apparatus at a predetermined timing corresponding to said injection of said medical liquid; and said imaging diagnostic apparatus returns one of said imaging order data received from said second computer according to said response request received from said first computer.

6. The fluoroscopic imaging system according to claim 2, wherein said imaging diagnostic apparatus and said first computer are connected to said second computer via a communication network;

said second computer manages a plurality of said imaging order data;

said imaging diagnostic apparatus transmits a response request for said imaging order data to said second computer with at least one order retrieval key;

said second computer selects and returns one of said plurality of imaging order data according to said response request received from said imaging diagnostic apparatus and said order retrieval key; and said imaging diagnostic apparatus transfers said imaging order data returned, to said first computer.

7. The fluoroscopic imaging system according to claim 1, wherein said injection history data comprises an injection job identity that is specific identification data of each injection job.

8. The fluoroscopic imaging system according to claim 1, wherein said injection history data comprises date and time to start and finish the injection.

9. The fluoroscopic imaging system according to claim 1, wherein said injection history data comprises identification data of the liquid injector that is used in the injection job.

10. The fluoroscopic imaging system according to claim 1, wherein said injection history data comprises identification data of the liquid and a region to be imaged.

11. The fluoroscopic imaging system according to claim 1, wherein said injection history data comprises image data of a time-based graph in which one of a horizontal axis and a vertical axis represents an elapsed time and the other represents an injection rate.

12. The fluoroscopic imaging system according to claim 1, wherein said liquid injector and said first computer are integrally constituted.

13. The fluoroscopic imaging system according to claim 1, wherein the first computer transmits, upon receipt of the injection history data from the liquid injector, a response request for the imaging order data to the second computer or the imaging diagnostic apparatus; and
    the second computer or the imaging diagnostic apparatus returns to the first computer the imaging order data selected when second computer or the imaging diagnostic apparatus receives the response request.

14. The fluoroscopic imaging system according to claim 1, wherein the first computer transmits a response request for the imaging order data to the second computer or the imaging diagnostic apparatus after a predetermined period of time from receipt of the injection history data; and
    the second computer or the imaging diagnostic apparatus returns to the first computer the imaging order data selected when the second computer or the imaging diagnostic apparatus receives the response request.

15. The fluoroscopic imaging system according to claim 1, wherein the liquid injector notifies the first computer of at least one of start or finish of the liquid injection;
    the first computer transmits, upon receipt of the notice of the start or finish of the liquid injection, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

16. The fluoroscopic imaging system according to claim 1, wherein the liquid injector notifies the first computer of at least one of start or finish of the liquid injection;
    the first computer transmits a response request for the imaging order data to the second computer or the imaging diagnostic apparatus after a predetermined period of time from receipt of the notice of the start or finish of the liquid injection; and
    the second computer or the imaging diagnostic apparatus returns to the first computer the imaging order data selected when the second computer or the imaging diagnostic apparatus receives the response request.

17. The fluoroscopic imaging system according to claim 1, wherein the liquid injector notifies the first computer of start of the liquid injection after a predetermined period of time from the start of the liquid injection;
    the first computer transmits, upon receipt of the notice of the start of the liquid injection from the liquid injector, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

18. The fluoroscopic imaging system according to claim 1, wherein the liquid injector notifies the first computer of finish of the liquid injection after a predetermined period of time from the finish of the liquid injection;
    the first computer transmits, upon receipt of the notice of the finish of the liquid injection from the liquid injector, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

19. The fluoroscopic imaging system according to claim 1, wherein the imaging diagnostic apparatus notifies the first computer of at least one of start or finish of imaging;
    the first computer transmits, upon receipt of the notice of the start or finish of imaging, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

20. The fluoroscopic imaging system according to claim 1, wherein the imaging diagnostic apparatus notifies the first computer of at least one of start or finish of imaging;
    the first computer transmits a response request for the imaging order data to the second computer or the imaging diagnostic apparatus after a predetermined period of time from receipt of the notice of the start or finish of imaging from the imaging diagnostic apparatus; and
    the second computer or the imaging diagnostic apparatus returns to the first computer the imaging order data selected when the second computer or the imaging diagnostic apparatus receives the response request.

21. The fluoroscopic imaging system according to claim 1, wherein the imaging diagnostic apparatus notifies the first computer of start of imaging after a predetermined period of time from the start of imaging;
    the first computer transmits, upon receipt of the notice of the start of imaging from the imaging diagnostic apparatus, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

22. The fluoroscopic imaging system according to claim 1, wherein the imaging diagnostic apparatus notifies the first computer of finish of imaging after a predetermined period of time from the finish of imaging;
    the first computer transmits, upon receipt of the notice of the finish of imaging from the imaging diagnostic apparatus, a response request for the imaging order data to the second computer or the imaging diagnostic apparatus; and
    the second computer or the imaging diagnostic apparatus returns to the first computer the imaging order data selected when the second computer or the imaging diagnostic apparatus receives the response request.

* * * * *